United States Patent [19]
Klimas

[11] Patent Number: 4,931,049
[45] Date of Patent: Jun. 5, 1990

[54] CATHETER COUPLING SYSTEM

[75] Inventor: David R. Klimas, Spring Valley, Calif.

[73] Assignee: Camino Laboratorties, Inc., San Diego, Calif.

[21] Appl. No.: 215,086

[22] Filed: Jul. 5, 1988

[51] Int. Cl.$^5$ .............................................. A61M 5/18
[52] U.S. Cl. ..................... 604/165; 604/83; 604/283
[58] Field of Search .................. 604/43–44, 604/48, 80–83, 158–169, 173, 256, 283, 905; 285/197

[56] References Cited

U.S. PATENT DOCUMENTS

| | | | |
|---|---|---|---|
| 3,399,674 | 9/1968 | Pannier et al. | 604/165 |
| 3,416,567 | 12/1968 | Dardel et al. | 604/83 X |
| 3,707,972 | 1/1973 | Villari et al. | 604/249 |
| 3,766,916 | 10/1973 | Moorehead et al. | 604/165 |
| 4,217,895 | 8/1980 | Sagae et al. | 604/44 |
| 4,737,145 | 4/1988 | Sharrow | 604/83 |
| 4,810,244 | 3/1989 | Allen | 604/44 |
| 4,819,637 | 4/1989 | Dormandy, Jr. et al. | 604/283 |
| 4,838,269 | 6/1989 | Robinson et al. | 604/165 |
| 4,857,062 | 8/1989 | Russell | 604/256 |

Primary Examiner—C. Fred Rosenbaum
Assistant Examiner—C. Maglione
Attorney, Agent, or Firm—Fulwider, Patton, Rieber, Lee & Utecht

[57] ABSTRACT

A catheter coupling system for connecting branch catheters to selected lumens of a multiple-lumen primary catheter. The system comprises a plurality of couplers each including a body having a primary passageway for receiving the primary catheter and a branch having a branch passageway for receiving one of the branch catheters. A fluid flow path between each branch catheter and the corresponding lumen in the primary catheter is established through an orifice in a side wall of the primary catheter which opens into the selected lumen and which is oriented adjacent a junction between the passageways in the coupler.

16 Claims, 1 Drawing Sheet

CATHETER COUPLING SYSTEM

BACKGROUND OF THE INVENTION

The present invention relates generally to medical catheters, and more particularly to a coupler for connecting branch catheters to a multi-lumen primary catheter.

Many modern medical devices utilize catheters which are inserted into a human body through an opening into a blood vessel and are then routed to a desired location such as the heart for the performance of a desired diagnostic or therapeutic procedure. As the procedures which can be carried out by means of such devices have become more sophisticated, the devices themselves have become more complex and today it is not uncommon for a single device to be capable of performing several functions simultaneously.

A catheter for use with such a medical device typically contains within a single outer sheath as many as five or six longitudinal pathways, or lumens, each of which can be used for a different purpose. For example, one such lumen might be used to extract a fluid from the body, another might be used to inject a drug, and a third might be used to carry compressed air to inflate a balloon on a distal tip of the catheter. Fluid-tight connections must be established between these lumens and external syringes or other devices which, for example, provide fluids to or receive fluids from the catheter.

The external devices to which the lumens in a multiple-lumen catheter must be connected typically terminate in single-lumen catheters. Accordingly, these single-lumen catheters must be connected to selected ones of the lumens in the multiple-lumen catheter. Various arrangements have been proposed for establishing such connections, but none of these arrangements has been completely satisfactory.

It will be apparent from the foregoing that there is a need for a simple, economical compact means to establish fluid-tight connections between the various lumens of a multiple-lumen catheter and corresponding single-lumen branch catheters.

SUMMARY OF THE INVENTION

The present invention provides a catheter coupling system including a plurality of one-piece couplers each of which connects a lumen in a branch catheter to a selected lumen in a multiple-lumen primary catheter through an orifice in a side wall of the primary catheter. Each coupler has a receptacle and a correspondingly-shaped projection for joining the couplers together into a simple, economical, compact catheter coupling system.

Briefly and in general terms, the coupler comprises a body defining a primary passageway sized to receive the primary catheter in close fitting relationship and a branch defining a branch passageway sized to receive the branch catheter in close fitting relationship. The branch passageway opens into the primary passageway at a junction. The primary catheter is oriented in its passageway with the orifice in its side wall adjacent the junction to establish a fluid flow path between the selected lumen and the lumen in the branch catheter.

In a more detailed aspect of a preferred embodiment of the invention, a first extremity of the body is shaped to define a projection through which the primary passageway extends and a second extremity of the body is shaped to define a receptacle into which the primary passageway opens. The receptacle has a shape complemental to the shape of the projection to permit a plurality of similar couplers to be assembled together by inserting the projection of one into the receptacle of another to define an extended primary passageway through the couplers. The couplers are joined together by, for example, friction fit or a bonding agent such as cement, glue or solvent, and the catheters are joined to the couplers in a fluid-tight relationship in a similar fashion.

The couplers are preferably arranged so as to locate the various branch passageways angularly about the primary passageway to facilitate communication between the branch catheters and the various lumens in the primary catheter.

An annular plug having an interior diameter sized to fit onto the primary catheter in close fitting relationship and an exterior diameter sized to fit into the receptacle in close fitting relationship is optionally used to couple the primary catheter tightly into the receptacle.

Other aspects and advantages of the present invention will become apparent from the following detailed description, taken in conjunction with the accompanying drawings, illustrating by way of example the principles of the invention.

DESCRIPTION OF THE PREFERRED EMBODIMENT

Figure 1:
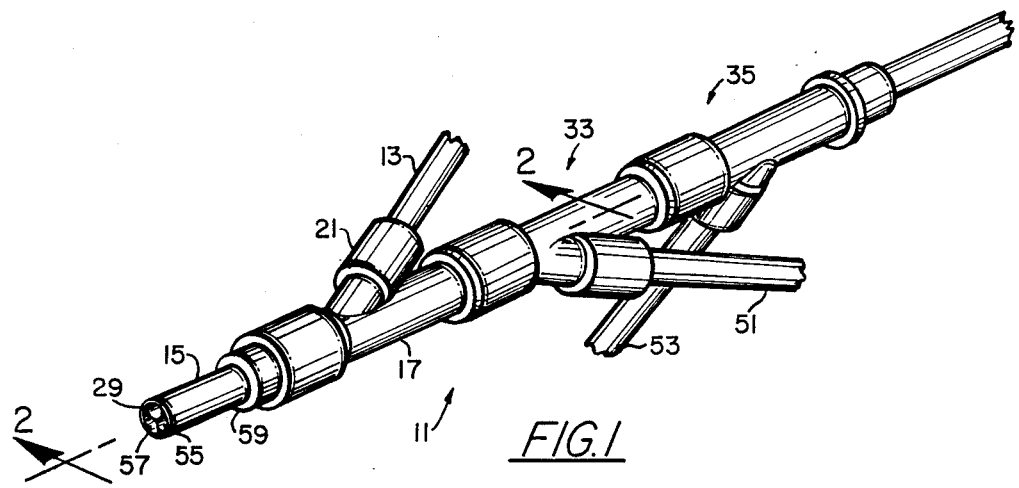
FIG. 1 is a perspective view of a catheter coupling system embodying the novel features of the invention.

As shown in the drawings for purposes of illustration, the invention is embodied in a novel catheter coupling system including a coupler 11 for coupling a branch catheter 13 to a primary multiple-lumen catheter 15. Various other arrangements have in the past been proposed for coupling branch catheters to a multiple-lumen primary catheter, but these have not been completely satisfactory.

In accordance with the invention, the coupler 11 includes a body 17 defining a primary passageway 19 which receives the primary catheter 15 and a branch 21 defining a branch passageway 23 which receives the branch catheter 13 and opens into the primary passageway 19 at a junction 25. An orifice 27 opening into a selected lumen 29 of the primary catheter 15 is located adjacent the junction 25 to establish a fluid flow path between the lumen 29 and a lumen 31 in the branch catheter 13. A plurality of additional similar couplings 33 and 35 are preferably interconnected with the coupling 11 to provide a simple, economical, compact catheter coupling system.

Figure 2:
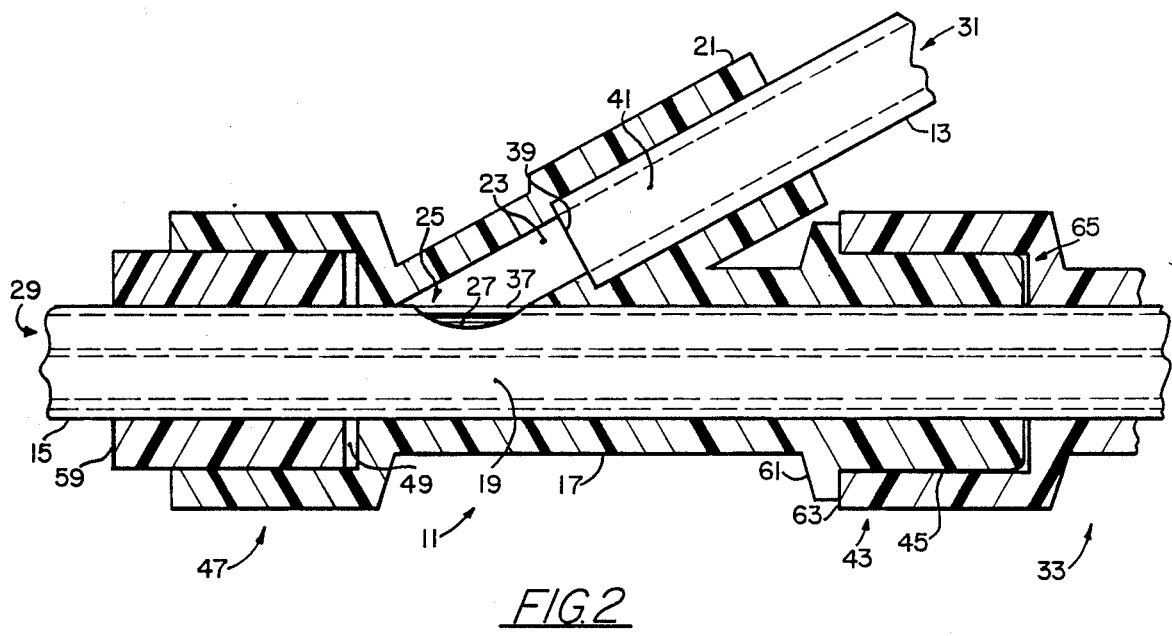
FIG. 2 is a sectional view taken along line 2—2 of FIG. 1.

As best shown in FIG. 2, the primary passageway 19 is defined longitudinally through the body 17 and is sized to receive the primary catheter 15 in close fitting relationship. The branch passageway 23 is defined through the branch 21 and is sized to receive the branch catheter 13 in close fitting relationship.

The fluid flow path between the lumens 29 and 31 extends from the lumen 29 through the orifice 27 which opens into the lumen 29 through a side wall 37 of the primary catheter 15, through the junction 25 into the branch passageway 23, and into the lumen 31 in the branch catheter 13 through an orifice 39 in an extremity 41 of the branch catheter 13. The primary catheter 15 is located in the primary passageway 19 with its orifice 27 adjacent the junction 25 and the branch catheter 13 is located in the branch passageway 23 with its orifice 39 adjacent the junction 25.

A first extremity 43 of the body 17 is preferably shaped to define a projection 45 through which the primary passageway 19 extends and a second extremity 47 of the body 17 is shaped to define a receptacle 49 into which the primary passageway 19 opens, the receptacle 49 having a shape complemental to the shape of the projection 45 whereby a plurality of similar couplers such as the couplers 33 and 35 can be assembled together by inserting the projection of one into the receptacle of another to define an extended primary passageway through the couplers.

A plurality of couplers 11, 33 and 35 which have thusly been assembled together define a catheter coupling system for coupling a plurality of branch catheters such as the catheter 13 and additional catheters 51 and 53 to the primary catheter 15 as best shown in FIG. 1. Separate fluid flow paths are thereby established between each of the branch catheters and selected ones of the lumens such as the lumen 29 and lumens 55 and 57, respectively, in the primary catheter 15.

Separate orifices are provided in the side wall 37 of the primary catheter 15 to establish separate flow paths between the lumens 29, 55 and 57 and their respective branch catheters. These orifices are spaced longitudinally apart from each other by predefined distances along the primary catheter, each such distance being approximately equal to the distance between the primary and branch passageway junctions in adjacent couplers.

The orifices in the primary catheter 15 are also arranged angularly about said catheter according to the relative locations of the lumens in the catheter, and the couplers 11, 33 and 35 are correspondingly oriented with the branch catheters extending in different directions from the primary catheter 15 such that an orifice in the extremity of each branch catheter is aligned with the corresponding orifice in the primary catheter 15.

The couplers 11, 33 and 35 are joined securely together by means such as friction fit or a bonding agent such as cement, glue or solvent. Similar means are also used to fix the primary catheter 15 and the branch catheters 13, 51 and 53 securely in their respective passageways and to prevent leaks from the fluid flow paths between the lumens 29, 55 and 57 in the primary catheter and the corresponding lumens in the branch catheters.

In a preferred embodiment an annular plug 59 having an interior diameter sized to fit onto the primary catheter 15 in close fitting relationship and an exterior diameter sized to fit into the receptacle 49 in close fitting relationship is provided to couple the primary catheter 15 tightly into the receptacle 49. Friction fit or a bonding agent may be used to secure the plug 59 and the catheter 15 into the receptacle 49.

An annular shoulder 61 is preferably defined in the body 17 adjacent the projection 45 for abutment against an extremity 63 of the adjacent coupler 33 when the projection 45 is inserted into a corresponding receptacle 65 of the coupler 33.

The coupler 11 can be molded of any of numerous kinds of plastic or the like, care being taken that the material from which the coupler is fabricated is chemically inert with respect to any drugs or bodily fluids that will pass through any of the catheters.

In an alternate embodiment (not shown) a primary passageway and a plurality of branches are molded in a single one-piece coupler to provide a coupling system structurally similar to that which results from joining a plurality of couplers together. Such a coupler is virtually identical to the coupling system described above except that it is formed in a single piece instead of in a plurality of pieces. A plurality of such one-piece coupling systems can be joined together just as the individual couplers can be joined together. However, although this one-piece coupling system offers the advantage of simpler construction, it does not afford as much flexibility as does a system comprising a plurality of separate couplers each having but one branch.

From the foregoing it will be appreciated that the coupling system of the invention provides a simple, economical, compact means for establishing secure connections between selected ones of the lumens in a multiple-lumen primary catheter and various branch catheters. A single coupler may be used to establish one such connection or a plurality of couplers may be assembled together into a single coupling system or may be molded in a single unit according to the number of branch catheters to be connected.

Although certain specific embodiments of the invention have been described and illustrated, the invention is not to be limited to the specific forms or arrangements of parts so described and illustrated, and various modifications and changes can be made without departing from the scope and spirit of the invention. Within the scope of the appended claims, therefore, the invention may be practiced otherwise than as specifically described and illustrated.

I claim:

1. A catheter coupler for coupling a branch catheter to a primary catheter having a plurality of lumens and for establishing a fluid flow path between a lumen in the branch catheter through an orifice in an extremity thereof and a selected one of a plurality of lumens in the primary catheter through an orifice in a side wall thereof, the coupler comprising:

a body for being mounted upon the primary catheter such that the orifice of the side wall of the primary catheter is disposed within the body and the primary catheter extends completely through the body, the body defining longitudinally therethrough a primary passageway sized to mount on the primary catheter in close fitting relationship, a branch defining therethrough a branch passageway opening into the primary passageway at a junction therebetween at the location of the orifice in the side wall of the primary catheter, and sized to receive the branch catheter in close fitting relationship, a fluid flow path being thereby established between the lumen in the branch catheter and the selected lumen in the primary catheter when the primary catheter is located in the primary passageway with its orifice adjacent the junction.

2. A coupler according to claim 1 wherein a first extremity of the body is shaped to define a projection through which the primary passageway extends and a second extremity of the body is shaped to define a receptacle into which the primary passageway opens, the receptacle having a shape complemental to the shape of the projection whereby a plurality of similar couplers can be assembled together by inserting the projection of one into the receptacle of another to define an extended primary passageway through the couplers.

3. A coupler according to claim 2 and further comprising an annular plug having an interior diameter sized to fit onto the primary catheter in close fitting relationship and an exterior diameter sized to fit into the receptacle in close fitting relationship and operative to couple the primary catheter tightly into the receptacle.

4. A catheter coupling system for coupling two branch catheters to a primary catheter and for establishing separate fluid flow paths between a lumen in the first branch catheter through an orifice in an extremity thereof and a first selected one of a plurality of lumens in the primary catheter through a first orifice in a side wall thereof and between a lumen in the second branch catheter through an orifice in an extremity thereof and a second selected lumen in the primary catheter through a second orifice in the side wall spaced longitudinally apart from the first orifice a predetermined distance, the system comprising:

a first coupler including a body for being mounted upon the primary catheter such that the primary catheter extends completely through the body, the body defining longitudinally therethrough a primary passageway sized to mount on the primary catheter in close fitting relationship and a branch defining therethrough a branch passageway opening into the primary passageway at a first junction located adjacent the first orifice of the primary catheter and sized to receive the first branch catheter in close fitting relationship;

a second coupler including a body for being mounted upon the primary catheter such that the primary catheter extends completely through the body, the body defining longitudinally therethrough a primary passageway sized to mount on the primary catheter in close fitting relationship and a branch defining therethrough a branch passage opening into the primary passageway opening into the primary passage way at a second junction located adjacent the second orifice of the primary catheter and sized to receive the second branch catheter in close fitting relationship; and means to join the couplers together with their primary passageways in communication with each other to define through the joined couplers an extended primary passageway, the junctions being separated from each other by the predetermined distance, separate fluid flow paths thereby being established between the lumen in the first branch catheter and the first lumen in the primary catheter and between the lumen in the second branch catheter and the second lumen in the primary catheter, respectively, when the primary catheter is located in the primary passageway with the first orifice adjacent the first junction and the second orifice adjacent the second junction and the first and second branch catheters are located in the first and second branch passageways with their orifices adjacent the first and second junctions, respectively.

5. A system according to claim 4 wherein the means to join the couplers together comprises a friction fit.

6. A system according to claim 4 wherein the means to join the couplers together comprises a bonding agent.

7. A system according to claim 4 wherein first extremities of the bodies of the couplers are shaped to define projections through which the primary passageways extend and second extremities of the bodies of the couplers are shaped to define receptacles into which the primary passageways open, the receptacles having a shape complemental to the shape of the projections whereby the couplers can be assembled together by inserting the projection of one into the receptacle of the other.

8. A system according to claim 7 and further comprising an annular plug having an interior diameter sized to fit onto the primary catheter in close fitting relationship and an exterior diameter sized to fit into one of the receptacles in close fitting relationship and operative to couple the primary catheter tightly into said receptacle.

9. A catheter coupling system for coupling two branch catheters to a primary catheter having a plurality of lumens and for establishing separate fluid flow paths between a lumen in the first branch catheter through an orifice in an extremity thereof and a first selected one of a plurality of lumens in the primary catheter through a first orifice in a side wall thereof and between a lumen in the second branch catheter through an orifice in an extremity thereof and a second selected lumen in the primary catheter through a second orifice in the side wall spaced longitudinally apart from the first orifice a predetermined distance, the system comprising:

a coupler including a body for being mounted upon the primary catheter such that the primary catheter extends completely through the body, the body defining longitudinally therethrough a primary passageway sized to receive the primary catheter in close fitting relationship, a first branch defining therethrough a first passageway opening into the primary passageway at a first junction located adjacent the first orifice in the primary catheter and sized to receive the first branch catheter in close fitting relationship, and a second branch defining therethrough a second branch passageway opening into the primary passageway at a second junction located adjacent the second orifice in the primary catheter and sized to receive the second branch catheter in close fitting relationship, the junctions being separated from each other by said predetermined distance, separate fluid flow paths being thereby established between the lumen in the first branch catheter and the first lumen in the primary catheter and between the lumen in the second branch catheter and the second lumen in the primary catheter, respectively, when the primary catheter is located in the primary passageway with the first orifice adjacent the second junction and the first and second branch passageways with their orifices adjacent the first and second junctions, respectively.

10. A system according to claim 9 wherein an extremity of the coupler is shaped to define a receptacle into which the primary passageway opens.

11. A system according to claim 10 and further comprising an annular plug having an interior diameter sized to fit onto the primary catheter in close fitting relationship and an exterior diameter sized to fit into the receptacle in close fitting relationship and operative to couple the primary catheter tightly into said receptacle.

12. A multiple lumen catheter system comprising:
a coupler including a body defining longitudinally therethrough a primary passageway sized to receive a primary catheter in close fitting relationship, a first branch defining therethrough a first branch passageway opening into the primary passageway at a first junction and sized to receive a first branch catheter in close fitting relationship, and a second branch defining therethrough a second branch passageway opening into the primary passageway at a second junction and sized to receive a second branch catheter in close fitting relationship, the junctions being separated from each other by a predetermined distance;

a primary catheter defining therein a plurality of lumens, a side wall of the catheter having a first orifice opening into a first one of the lumens and a second orifice opening into a second one of the lumens and spaced longitudinally apart from the first orifice by said predetermined distance, the primary catheter being located in the primary passageway with the first orifice adjacent the first junction and the second orifice adjacent the second junction;

first and second branch catheters, each said catheter defining therein a lumen, an extremity of each branch catheter having an orifice opening into its lumen, the catheters being located in the first and second branch passageways with their orifices adjacent the first and second junctions, respectively; and means to join the catheters and the body together to define a first leakproof fluid flow path between the first lumen in the primary catheter and the lumen in the first branch catheter and between the second lumen in the primary catheter and the lumen in the second branch catheter.

13. A system according to claim 12 wherein an extremity of the coupler is shaped to define a receptacle into which the primary passageway opens.

14. A system according to claim 13 and further comprising an annular plug having an interior diameter sized to fit onto the primary catheter in close fitting relationship and an exterior diameter sized to fit into the receptacle in close fitting relationship and operative to couple the primary catheter tightly into said receptacle.

15. A system according to claim 12 wherein the means to join the catheters and the body together comprises a friction fit.

16. A system according to claim 12 wherein the means to join the catheters and the body together comprises a bonding agent.

* * * * *

UNITED STATES PATENT AND TRADEMARK OFFICE
CERTIFICATE OF CORRECTION

PATENT NO. : 4,931,049
DATED : June 5, 1990
INVENTOR(S) : David R. Klimas

It is certified that error appears in the above-identified patent and that said Letters Patent is hereby corrected as shown below:

In Claim 4, Column 5, line 39, replace "passage" with --passageway--.

In Claim 9, Column 6, line 34, between "first" and "passageway" insert --branch--.

Signed and Sealed this

Twenty-seventh Day of August, 1991

Attest:

HARRY F. MANBECK, JR.

*Attesting Officer*  *Commissioner of Patents and Trademarks*